(12) United States Patent  
Klein et al.

(10) Patent No.: US 8,709,049 B2  
(45) Date of Patent: Apr. 29, 2014

(54) FASTENER ASSEMBLY THAT FASTENS TO POLYAXIAL PEDICLE SCREW

(75) Inventors: Assaf Klein, Kibbutz Hama'apil (IL); Eyal Zilberberg, Kfar Yona (IL)

(73) Assignee: Premia Spine Ltd., Ramat Poleg (IL)

( * ) Notice: Subject to any disclaimer, the term of this patent is extended or adjusted under 35 U.S.C. 154(b) by 0 days.

(21) Appl. No.: 13/602,434

(22) Filed: Sep. 4, 2012

(65) Prior Publication Data

US 2012/0330363 A1     Dec. 27, 2012

Related U.S. Application Data

(63) Continuation of application No. 12/244,781, filed on Oct. 3, 2008, now abandoned.

(51) Int. Cl.
*A61B 17/70* (2006.01)

(52) U.S. Cl.
USPC ........... 606/266; 606/264; 606/265; 606/259; 606/86 A

(58) Field of Classification Search
USPC ................................ 606/246–278, 86 A, 914
See application file for complete search history.

(56) References Cited

U.S. PATENT DOCUMENTS

| | | | |
|---|---|---|---|
| 2005/0102028 A1* | 5/2005 | Arnin et al. | 623/17.13 |
| 2006/0064091 A1* | 3/2006 | Ludwig et al. | 606/61 |
| 2006/0142759 A1* | 6/2006 | Arnin et al. | 606/61 |
| 2008/0021464 A1* | 1/2008 | Morin et al. | 606/61 |
| 2008/0294194 A1* | 11/2008 | Capote et al. | 606/246 |
| 2008/0319483 A1* | 12/2008 | Triplett et al. | 606/246 |
| 2009/0216276 A1* | 8/2009 | Pasquet | 606/249 |
| 2010/0094345 A1* | 4/2010 | Saidha et al. | 606/250 |

* cited by examiner

*Primary Examiner* — Jan Christopher Merene
(74) *Attorney, Agent, or Firm* — Dekel Patent Ltd.; David Klein

(57) ABSTRACT

A fastener assembly including an existing polyaxial pedicle screw that has been previously installed in a spinal structure, the polyaxial pedicle screw including a polyaxial head to which a prosthetic member is secured, a fastening portion fastened to the polyaxial head over the prosthetic member, and a connector element that extends from the fastening portion, the connector element being connected to another spinal structure.

4 Claims, 18 Drawing Sheets

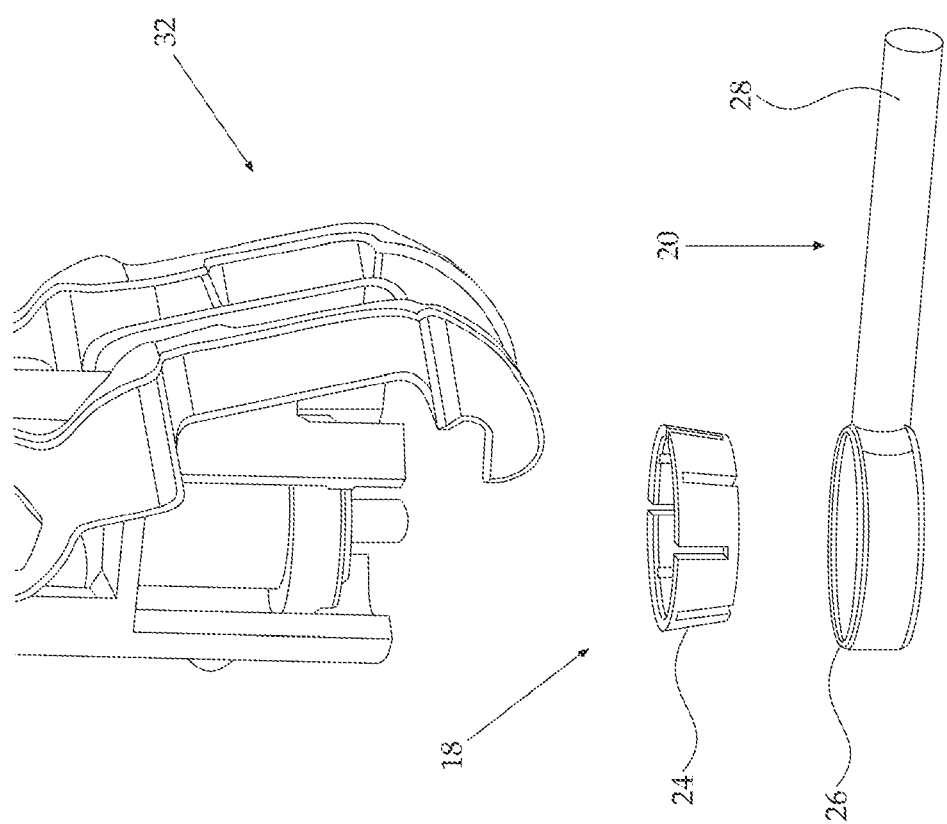

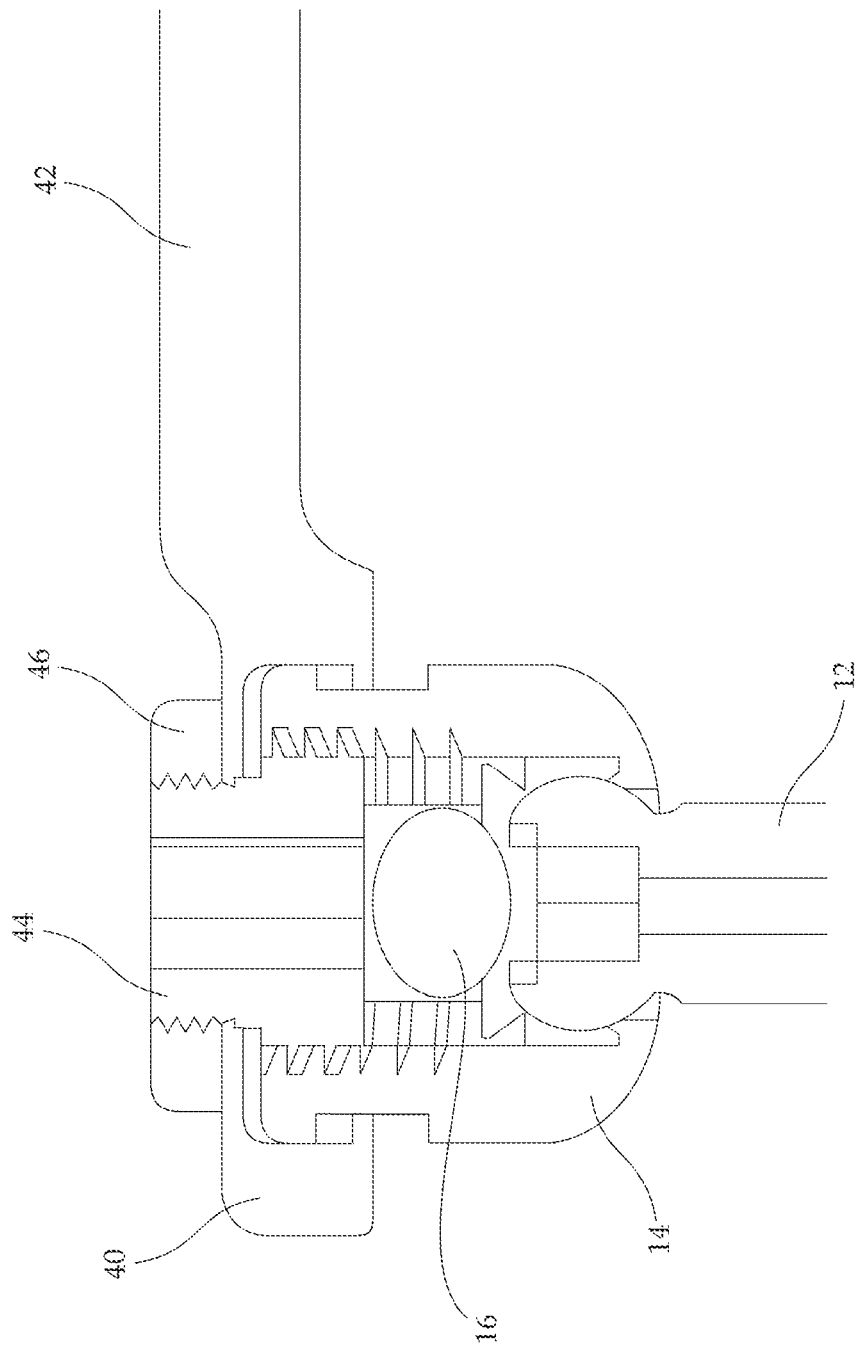

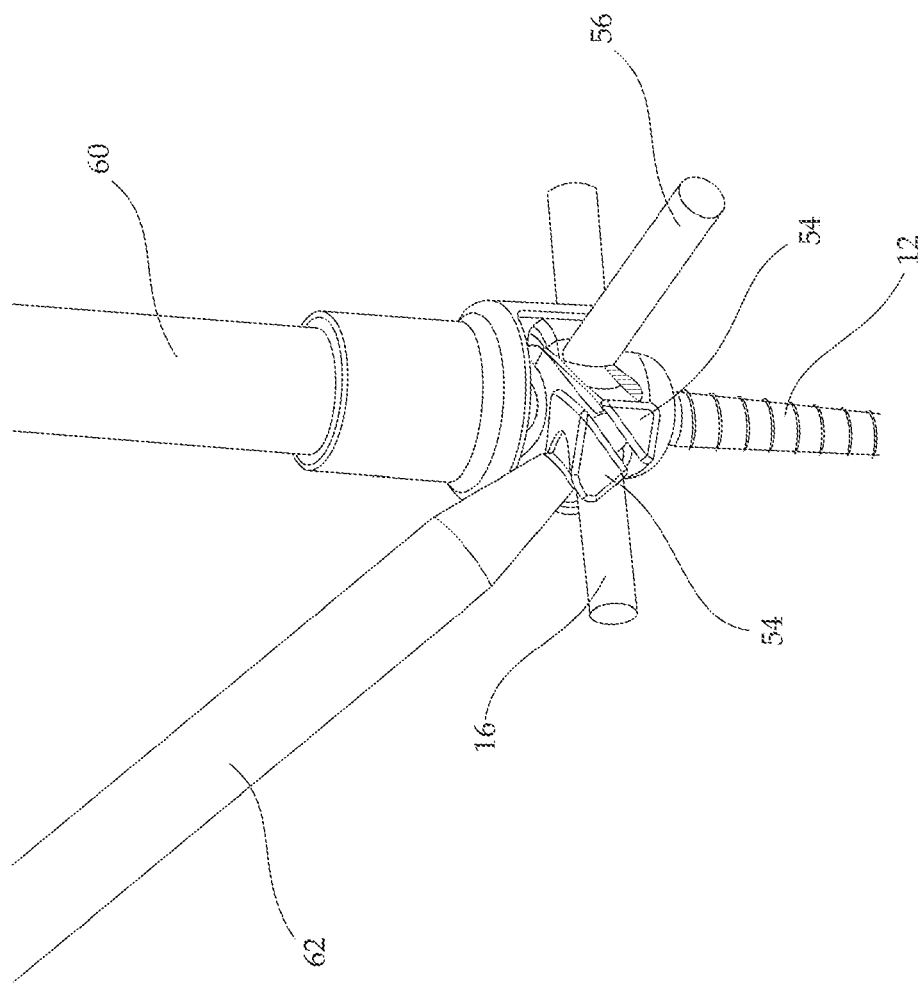

FASTENER ASSEMBLY THAT FASTENS TO POLYAXIAL PEDICLE SCREW

CROSS REFERENCE TO OTHER APPLICATIONS

This application is a continuation of U.S. patent application Ser. No. 12/244,781, filed Oct. 3, 2008, now abandoned, and claims priority therefrom.

FIELD OF THE INVENTION

This invention relates generally to polyaxial fasteners, such as a polyaxial pedicle screw assembly, and particularly to a fastener assembly that fastens to polyaxial pedicle screws that have already been installed in spinal structure.

BACKGROUND OF THE INVENTION

Polyaxial pedicle screw assemblies are well known in the art and may be used for connecting vertebrae or other spinal structure to rods in spinal surgery. For example, polyaxial pedicle screw assemblies are known that incorporate a ball joint at the connection to the rod to allow the surgeon some flexibility in placing the screws. Tightening a nut on the screw compresses the ball joint components to lock the angular position of the ball joint.

SUMMARY OF THE INVENTION

The present invention seeks to provide a fastener assembly that fastens to polyaxial pedicle screws that have already been installed in spinal structure, as is described more in detail hereinbelow. The fastener assembly of the present invention may be used to fasten different elements to the pedicle screws, such as but not limited to, fusion rods between adjoining vertebrae or crossbars and other connections from the pedicle screws to any suitable portion of the spine in the patient.

The present invention provides the possibility of connecting with cross connectors to fusion systems directly to the pedicle screw and not between the fusion rods as in current prior art systems.

There is thus provided in accordance with an embodiment of the invention a fastener assembly including an existing polyaxial pedicle screw that has been previously installed in a spinal structure, the polyaxial pedicle screw including a polyaxial head to which a prosthetic member is secured, a fastening portion fastened to the polyaxial head over the prosthetic member, and a connector element that extends from the fastening portion, the connector element being connected to another spinal structure.

In accordance with an embodiment of the invention the fastening portion includes a wedge ring and the connector element includes a conical ring into which the wedge ring fits, the connector element including a connecting member that extends from the conical ring, wherein the wedge ring is sized to fit over the polyaxial head and the conical ring wedges the wedge ring onto the polyaxial head.

Further in accordance with an embodiment of the invention the wedge ring has a conical periphery with a top surface that has a larger outer diameter than a bottom surface thereof, and the conical ring has a top surface with a larger inner diameter than a bottom surface thereof, the larger outer diameter not being greater than the larger inner diameter. A plurality of grooves may be formed in the conical periphery of the wedge ring. One or more of the grooves may be open at the top surface and closed at the bottom surface and one or more other grooves may be closed at the top surface and open at the bottom surface.

In accordance with another embodiment of the invention the fastening portion includes a closed ring and the connector element includes a connecting member that extends from the closed ring, and wherein the existing polyaxial pedicle screw includes a first mechanical fastener fastened to the polyaxial head, wherein the closed ring is placed over the first mechanical fastener such that the first mechanical fastener protrudes through the closed ring, and further including a second mechanical fastener that fastens to the first mechanical fastener and is tightened against the closed ring.

In accordance with yet another embodiment of the invention the fastening portion includes an open ring that fits over the polyaxial head and a mechanical fastener that fastens end portions of the open ring towards each other so as to clamp the open ring onto the polyaxial head, and the connector element includes a connecting member that extends from the open ring. The end portions of the open ring can be angled at an acute angle with respect to a top surface of the open ring.

There is also provided in accordance with an embodiment of the invention a method including fastening a fastening assembly to a polyaxial head of an existing polyaxial pedicle screw that has been previously installed in a spinal structure, a prosthetic member being secured to the polyaxial head, wherein the fastening assembly includes a fastening portion fastened to the polyaxial head over the prosthetic member and a connector element that extends from the fastening portion, and connecting the connector element to another spinal structure.

BRIEF DESCRIPTION OF THE DRAWINGS

The present invention will be understood and appreciated more fully from the following detailed description taken in conjunction with the drawings in which:

FIG. 3A is an exploded illustration of the wedge ring, the connector element and a fastening tool used to secure the fastener assembly on an existing polyaxial pedicle screw, in accordance with an embodiment of the present invention;

FIG. 5 is a partially sectional illustration of the closed ring and connector element of FIG. 4;

FIG. 9E is a pictorial illustration of tightening a set screw of the fastener assembly of FIG. 7 on the existing polyaxial pedicle screw.

DETAILED DESCRIPTION OF EMBODIMENTS

Figure 1:
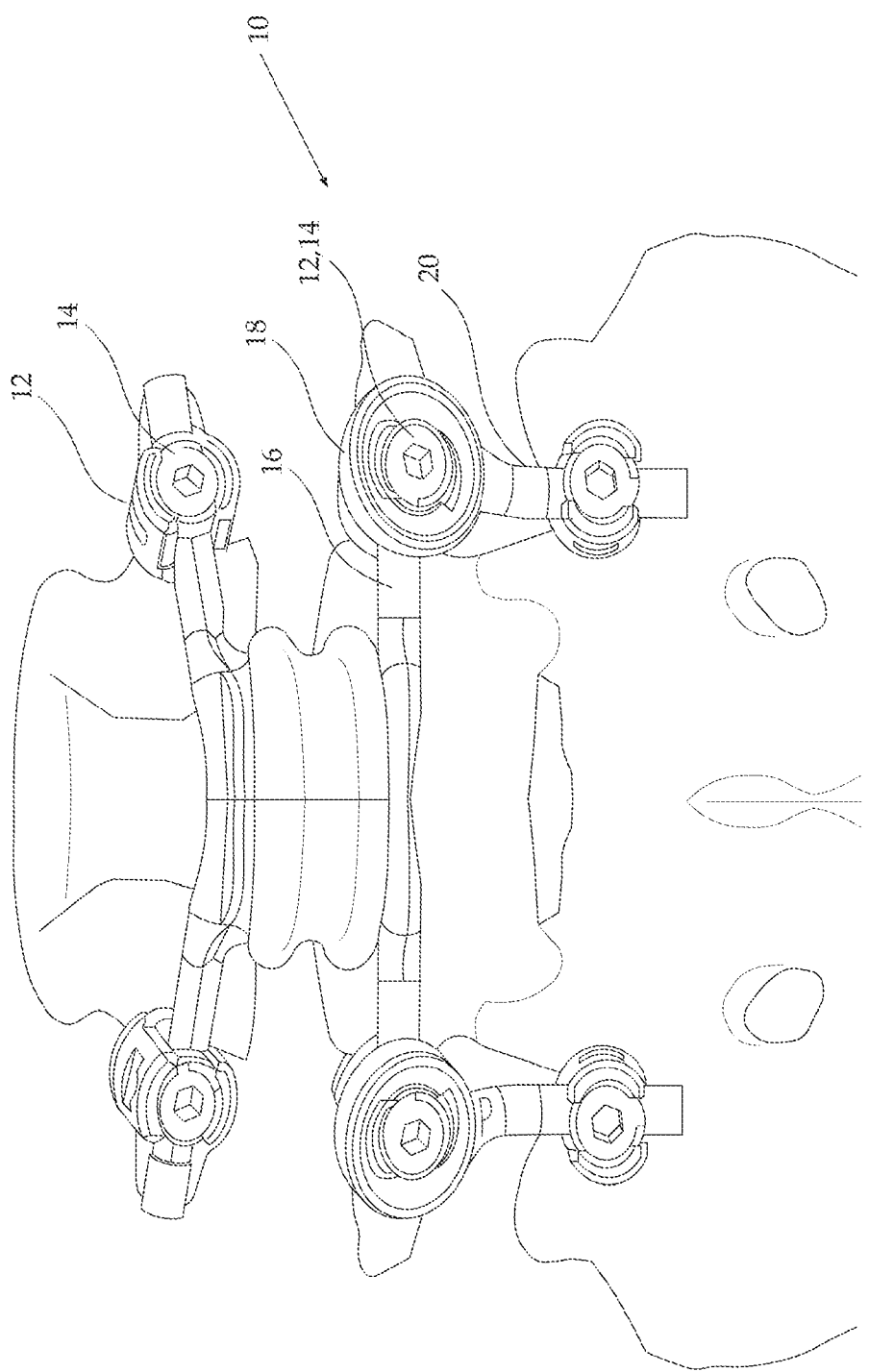
FIG. 1 is a simplified pictorial illustration of a fastener assembly, constructed and operative in accordance with an embodiment of the present invention, showing two such fastener assemblies with wedge rings and connector elements secured to polyaxial pedicle screw heads that have previously been installed in the left and right sides of vertebra.

Reference is now made to FIG. 1, which illustrates a fastener assembly 10, constructed and operative in accordance with a non-limiting embodiment of the present invention.

Fastener assembly 10 includes one or more existing polyaxial pedicle screws 12 (in the illustrated embodiment left and right screws are shown) that have been previously installed in a spinal structure (e.g., pedicles, articular processes, etc.). The polyaxial pedicle screw 12 includes a polyaxial head 14 to which a prosthetic member 16 is secured. In the non-limiting illustrated embodiment, prosthetic member 16 are the prongs of a TOPS (total posterior spine implant) brand spinal prosthesis, commercially available from the present assignee and described in U.S. Pat. No. 7,011,685, the disclosure of which is incorporated herein by reference.

Figure 2A:
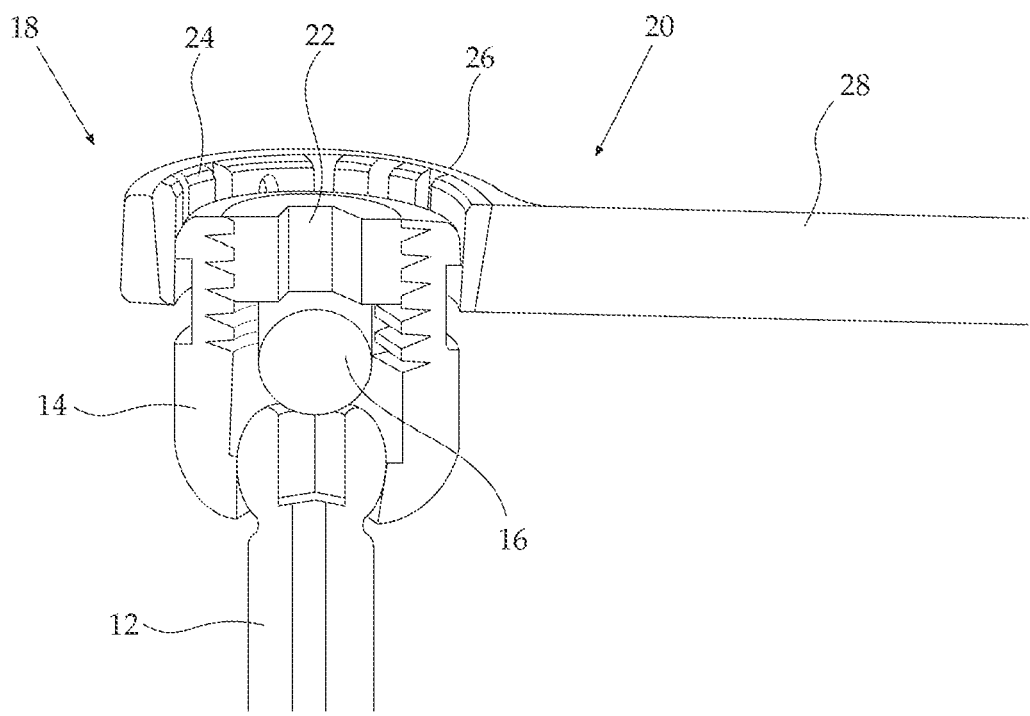
FIGS. 2A and 2B are partially sectional illustrations of the wedge ring and connector element of FIG. 1.
Figure 2B:
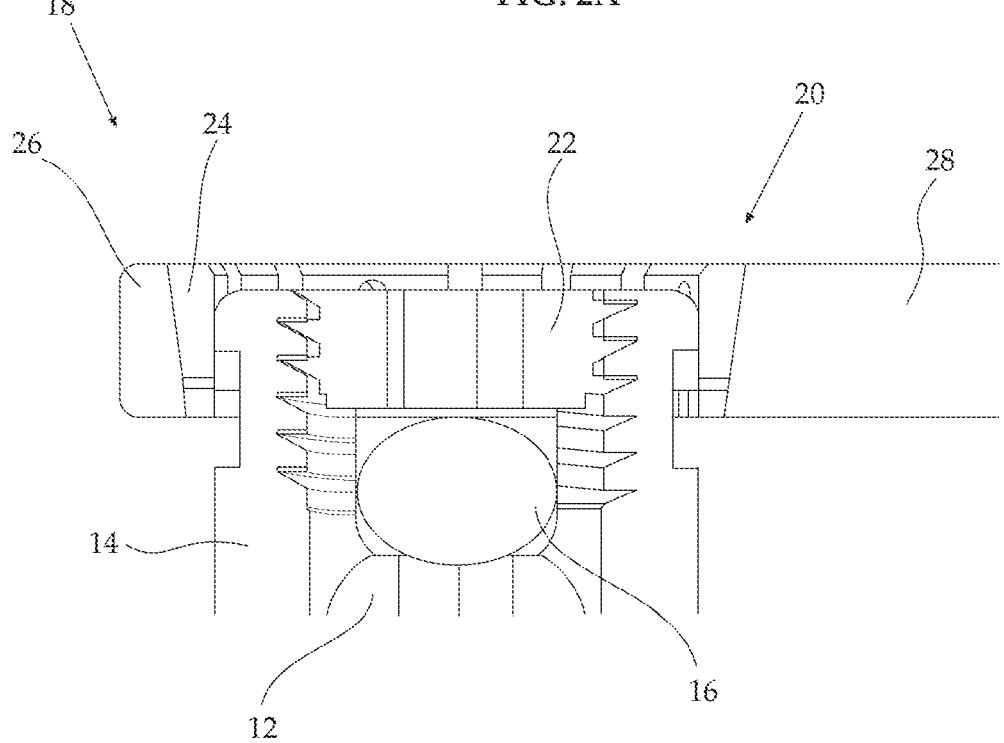

Reference is now made to FIGS. 2A and 2B. A set screw 22 is screwed in the female threads of polyaxial head 14 and clamps down on prosthetic member 16. A fastening portion 18 (described more in detail below) is fastened to the polyaxial head 14 over the prosthetic member 16. A connector element 20 extends from fastening portion 18. As seen in FIG. 1, connector element 20 is connected to another spinal structure (e.g., adjacent lumbar vertebra).

In accordance with an embodiment of the invention, fastening portion 18 includes a wedge ring 24 and connector element 20 includes a conical ring 26 into which wedge ring 24 fits. Connector element 20 includes a connecting member 28 that extends from conical ring 26, such as a rod, bar, plate and the like. Wedge ring 24 is sized to fit over polyaxial head 14 and conical ring 26 wedges wedge ring 24 onto polyaxial head 14.

As seen in FIG. 2B, wedge ring 24 has a conical periphery with a top surface that has a larger outer diameter than a bottom surface thereof, and conical ring 26 has a top surface with a larger inner diameter than a bottom surface thereof, the larger outer diameter of wedge ring 24 not being greater than the larger inner diameter of conical ring 26. As seen in FIG. 3A, a plurality of grooves 30 may be formed in the conical periphery of wedge ring 24. One or more of the grooves 30 may be open at the top surface and closed at the bottom surface and one or more other grooves 30 may be closed at the top surface and open at the bottom surface.

The fastener assemblies of the present invention may be constructed of any suitable, rigid, medically safe material, such as but not limited to, stainless steel alloy (e.g., AISI 316L), titanium or titanium alloy or chrome cobalt alloy, PEEK, shape memory alloys or polymers, and any combination thereof.

Reference is now made to FIGS. 3A-3F, which illustrate installing wedge ring 24 and connector element 20 on the pedicle screw 12.

Figure 3B:
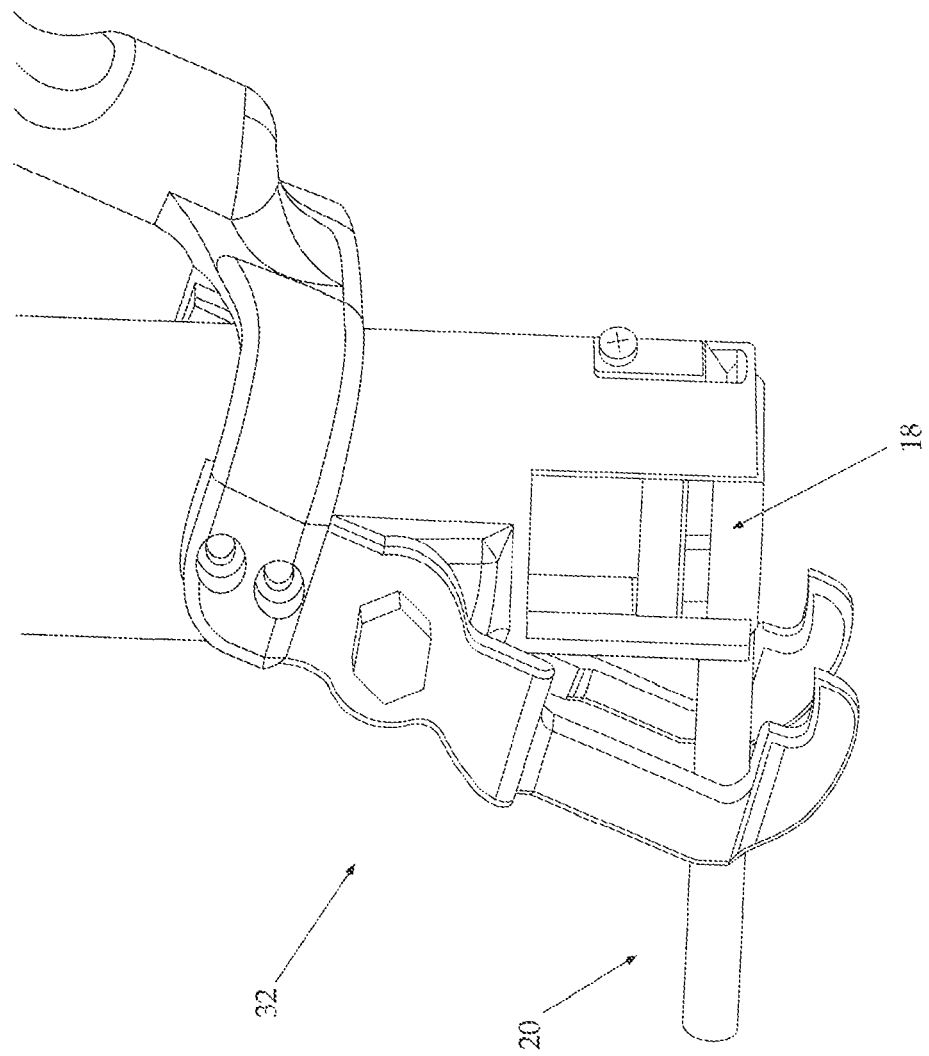
FIG. 3B is a pictorial illustration of the wedge ring and connector element mounted in the fastening tool.
Figure 3D:
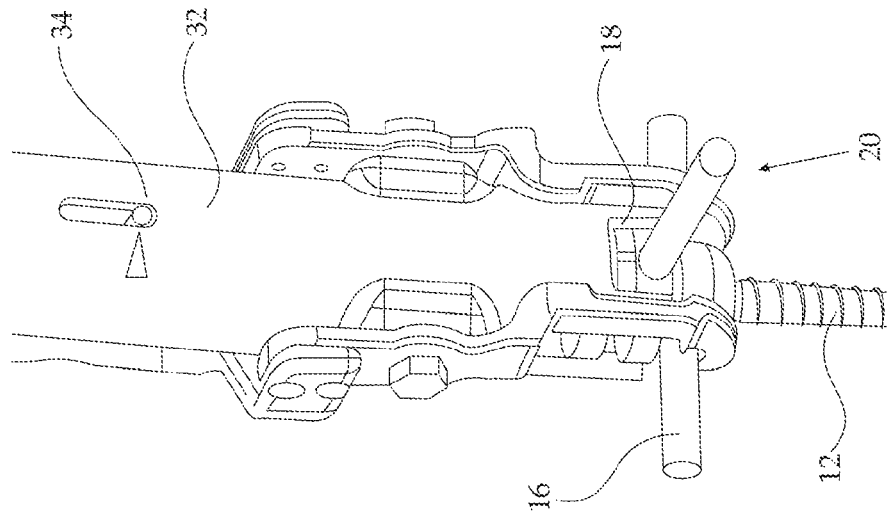
FIGS. 3C and 3D are pictorial illustrations of the fastening tool with the wedge ring and connector element placed over the existing polyaxial pedicle screw.
Figure 3C:
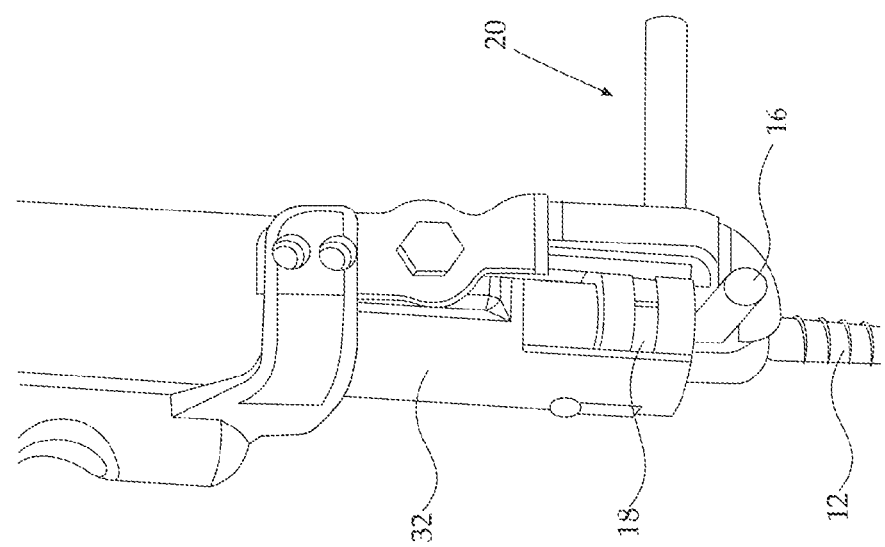

A fastening tool 32 is used to secure the fastener assembly on the existing polyaxial pedicle screw. FIGS. 3A and 3B show wedge ring 24 and connector element 20 inserted in jaws of fastening tool 32. FIGS. 3C and 3D show fastening tool 32 with wedge ring 24 and connector element 20 placed over the existing polyaxial pedicle screw 14. The fastening tool 32 has an alignment indicator 34 that indicates the proper alignment of connector element 20 with the existing prosthetic member 16.

Figure 3F:
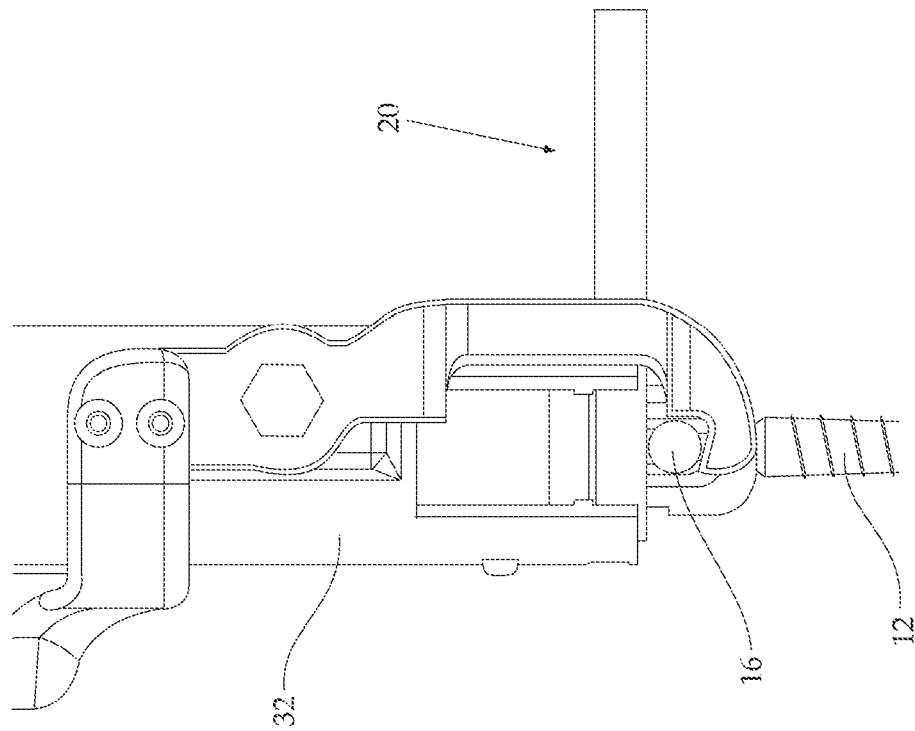
FIGS. 3E and 3F are pictorial illustrations of using the fastening tool to secure the fastening assembly of FIG. 1 on to the existing polyaxial pedicle screw.
Figure 3E:
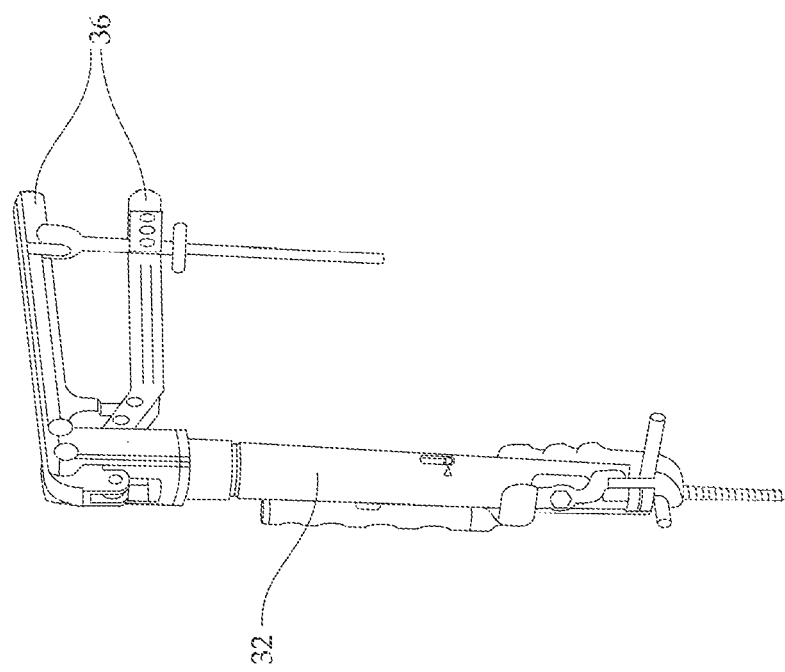

FIGS. 3E and 3F show using the fastening tool 32 to secure fastening assembly 10 on to the existing polyaxial pedicle screw 10. Handles 36 of fastening tool 32 may be squeezed so that conical ring 26 wedges wedge ring 24 onto polyaxial head 14 as described above with reference to FIGS. 2A-2B.

The set screw of the existing pedicle screw may be left loose or loosened somewhat during installation of the fastener assembly on the existing polyaxial pedicle screw and afterwards tightened to the recommended torque.

Figure 4:
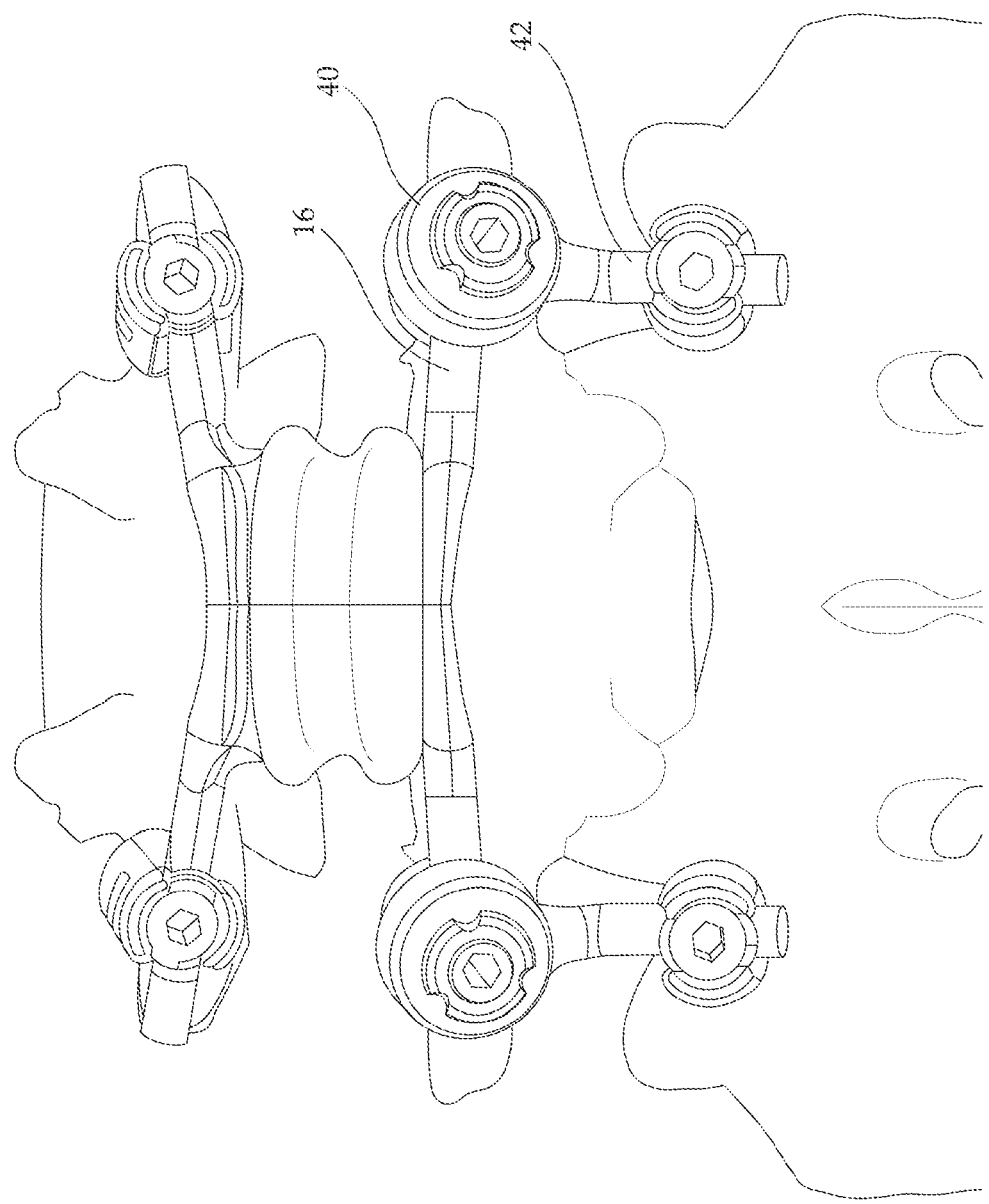
FIG. 4 is a simplified pictorial illustration of a fastener assembly, constructed and operative in accordance with another embodiment of the present invention, showing two such fastener assemblies with closed rings and connector elements secured to polyaxial pedicle screw heads that have previously been installed in the left and right sides of vertebra.

Reference is now made to FIGS. 4 and 5. In accordance with another embodiment of the invention the fastening portion of the fastening assembly includes a closed ring 40 and the connector element includes a connecting member 42 that extends from closed ring 40. The existing polyaxial pedicle screw 12 includes a first mechanical fastener 44 (such as but not limited to, an elongate set screw with a central through hole) fastened to polyaxial head 14. Closed ring 40 is placed over the first mechanical fastener 44 such that the first mechanical fastener 44 protrudes through closed ring 40. A second mechanical fastener 46 (such as but not limited to, a nut) fastens to the first mechanical fastener 44 and is tightened against closed ring 40, thereby securing the fastening portion of the fastening assembly to the existing polyaxial pedicle screw 12.

Figure 6A:
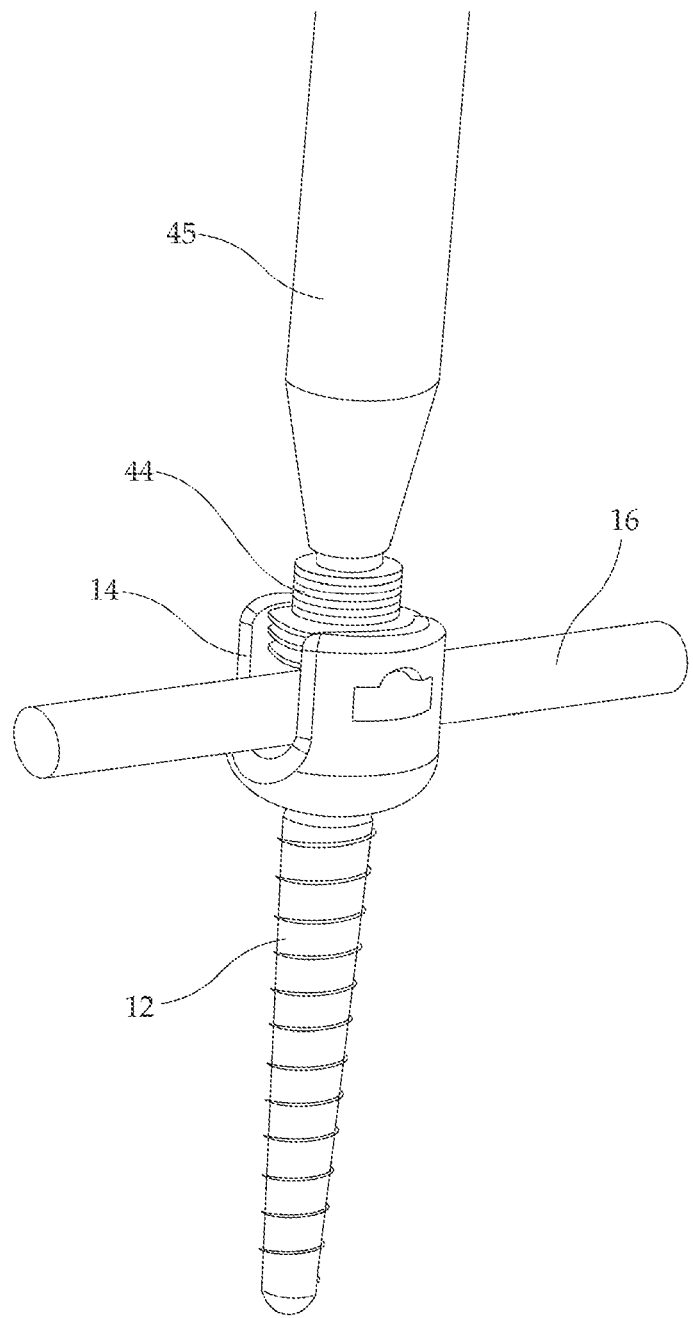
FIG. 6A is a pictorial illustration of fastening a set screw of the fastener assembly of FIG. 4 on an existing polyaxial pedicle screw, in accordance with an embodiment of the present invention.
Figure 6B:
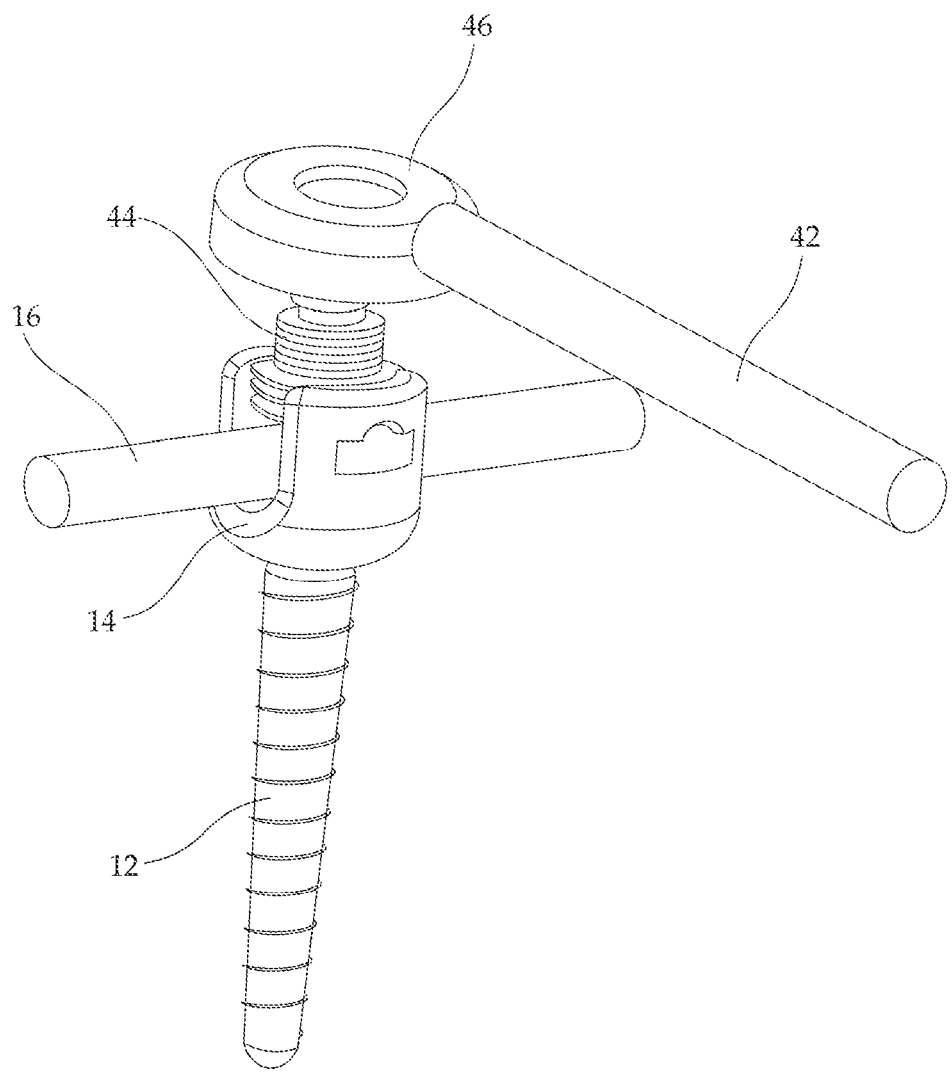
FIG. 6B is a pictorial illustration of placing the connector element of the fastener assembly of FIG. 4 on the set screw.

Reference is now made to FIGS. 6A-6F. In FIG. 6A, a tool 45 is used to screw the first mechanical fastener 44 on the polyaxial head 14 against the prosthetic member 16. In FIG. 6B, the closed ring 40 of the connector element is placed over first mechanical fastener 44 (first mechanical fastener 44 goes through the hole of the closed ring 40). The first mechanical fastener 44 may be further tightened a little at this time.

Figure 6D:
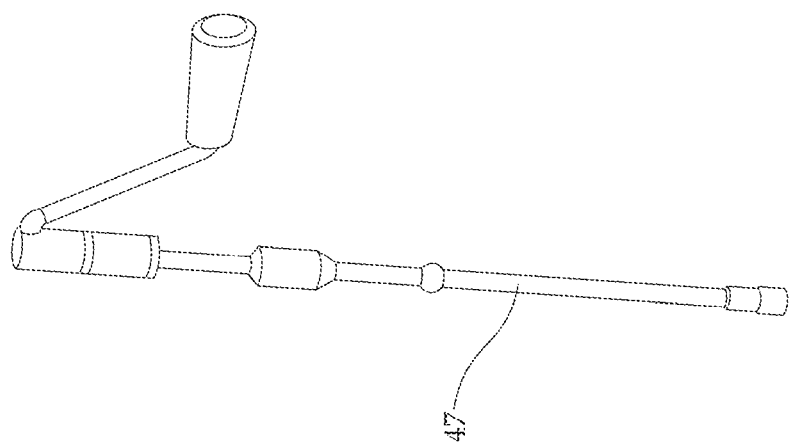
FIGS. 6C and 6D are pictorial illustrations of a nut of the fastener assembly of FIG. 4 mounted in a fastening tool used to secure the fastener assembly on an existing polyaxial pedicle screw, in accordance with an embodiment of the present invention.
Figure 6C:
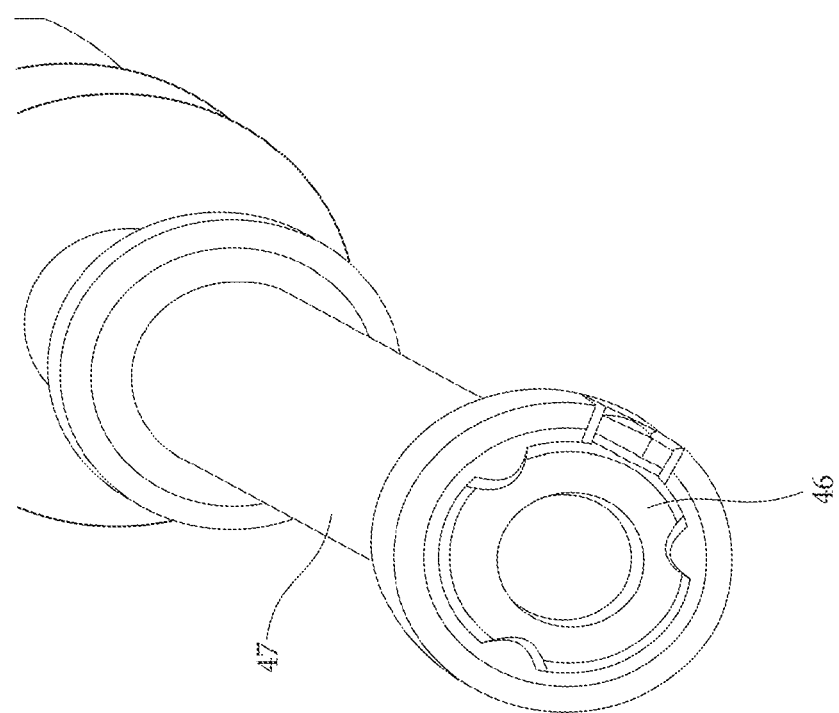
Figure 6E:
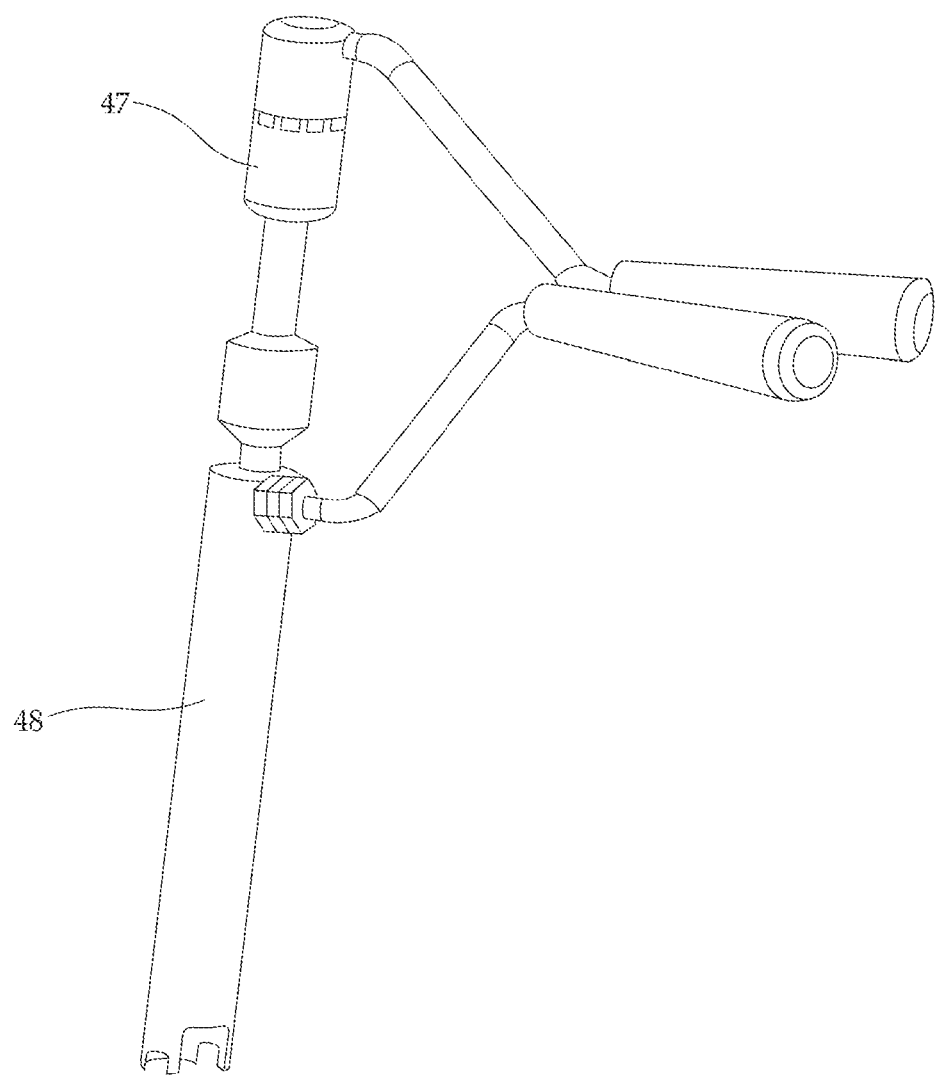
FIG. 6E is a pictorial illustration of feeding a torque handle through a counter torque handle of the fastening tool.
Figure 6F:
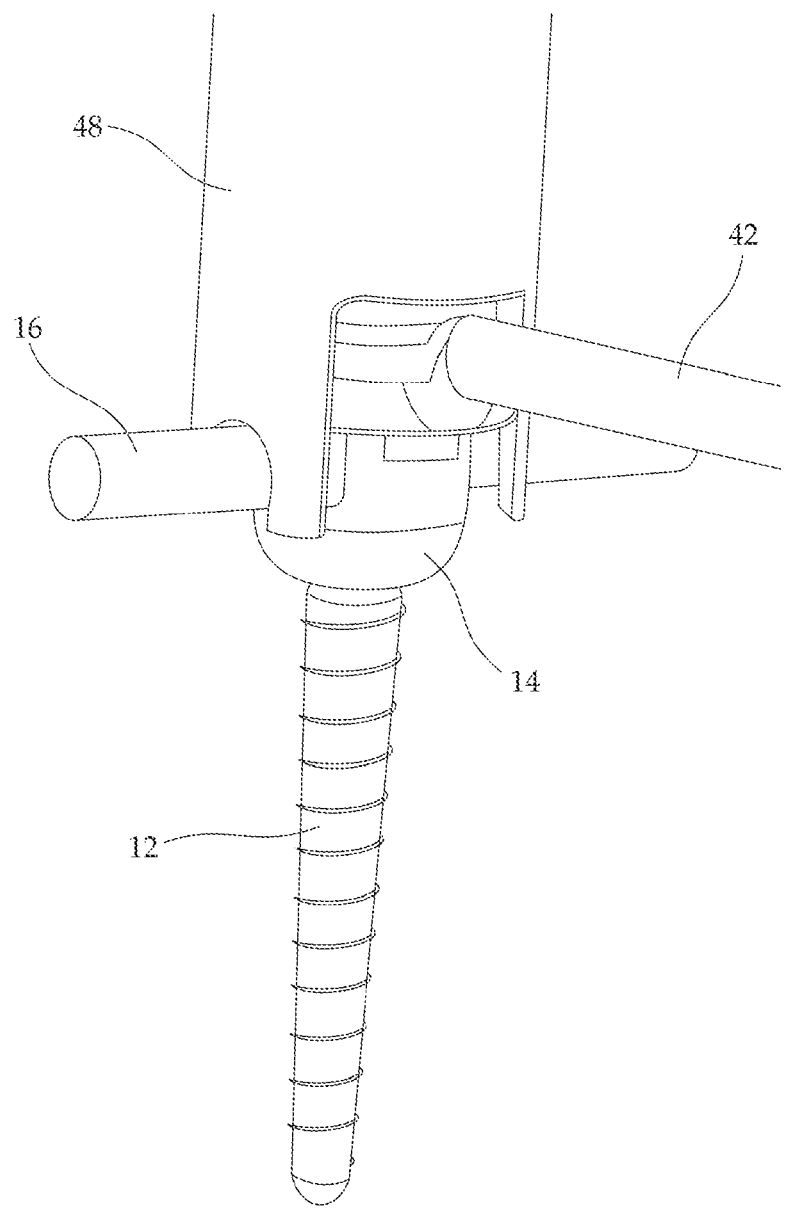
FIG. 6F is a pictorial illustration of using the fastening tool to secure the fastening assembly of FIG. 4 on to the existing polyaxial pedicle screw.

FIGS. 6C and 6D illustrate second mechanical fastener 46 mounted in a fastening tool (torque handle tool) 47 used to secure the fastener assembly on the existing polyaxial pedicle screw. FIG. 6E illustrates feeding the torque handle tool 47 through a counter torque handle 48. As seen in FIG. 6F, the counter torque handle 48 is used to hold the fastening assembly in proper alignment on the existing polyaxial pedicle screw 12. Torque handle tool 47 is used to tighten second mechanical fastener 46 against closed ring 40, thereby securing the fastening portion of the fastening assembly to the existing polyaxial pedicle screw 12.

Figure 7:
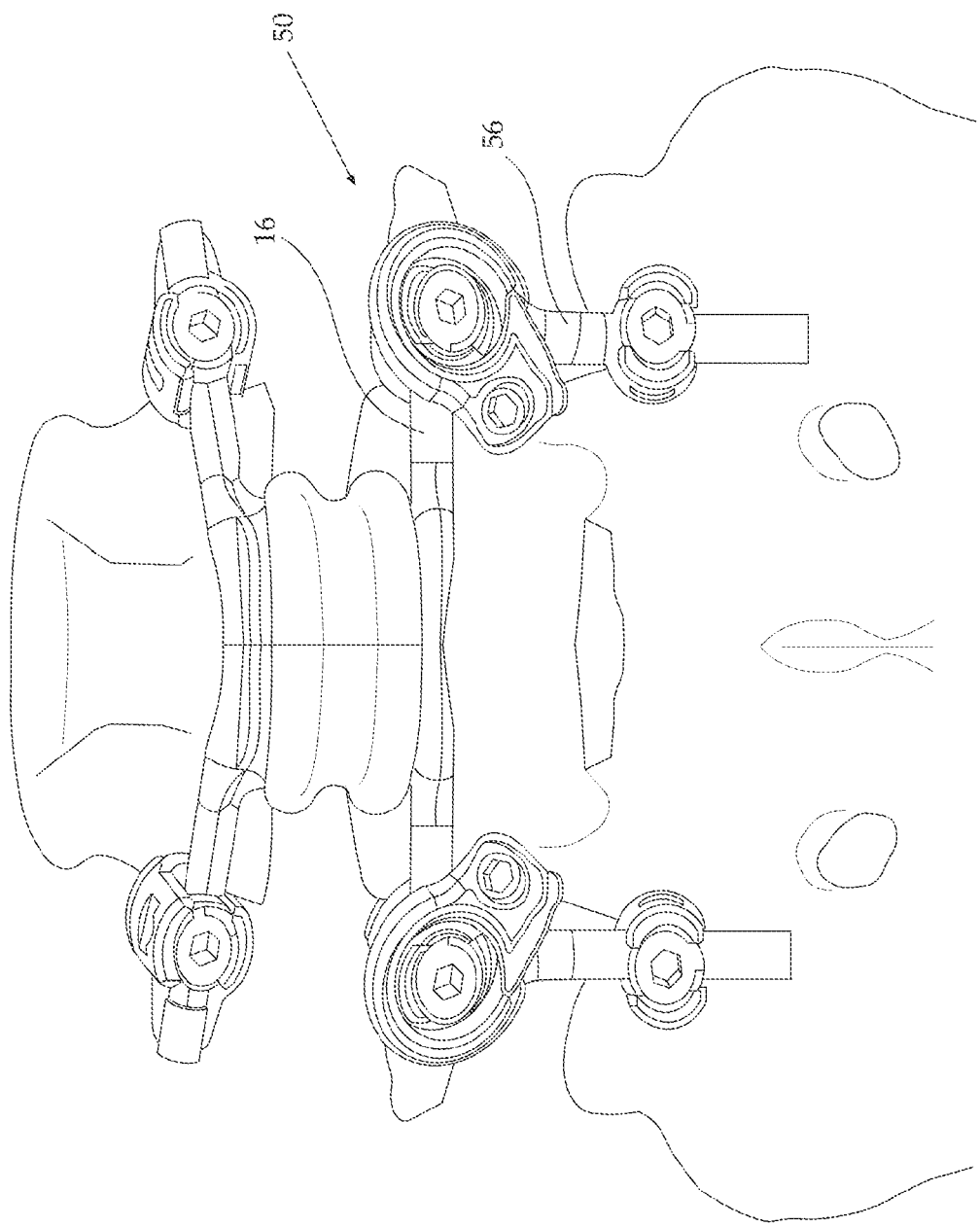
FIG. 7 is a simplified pictorial illustration of a fastener assembly, constructed and operative in accordance with yet another embodiment of the present invention, showing two such fastener assemblies with open rings and connector elements secured to polyaxial pedicle screw heads that have previously been installed in the left and right sides of vertebra.
Figure 8:
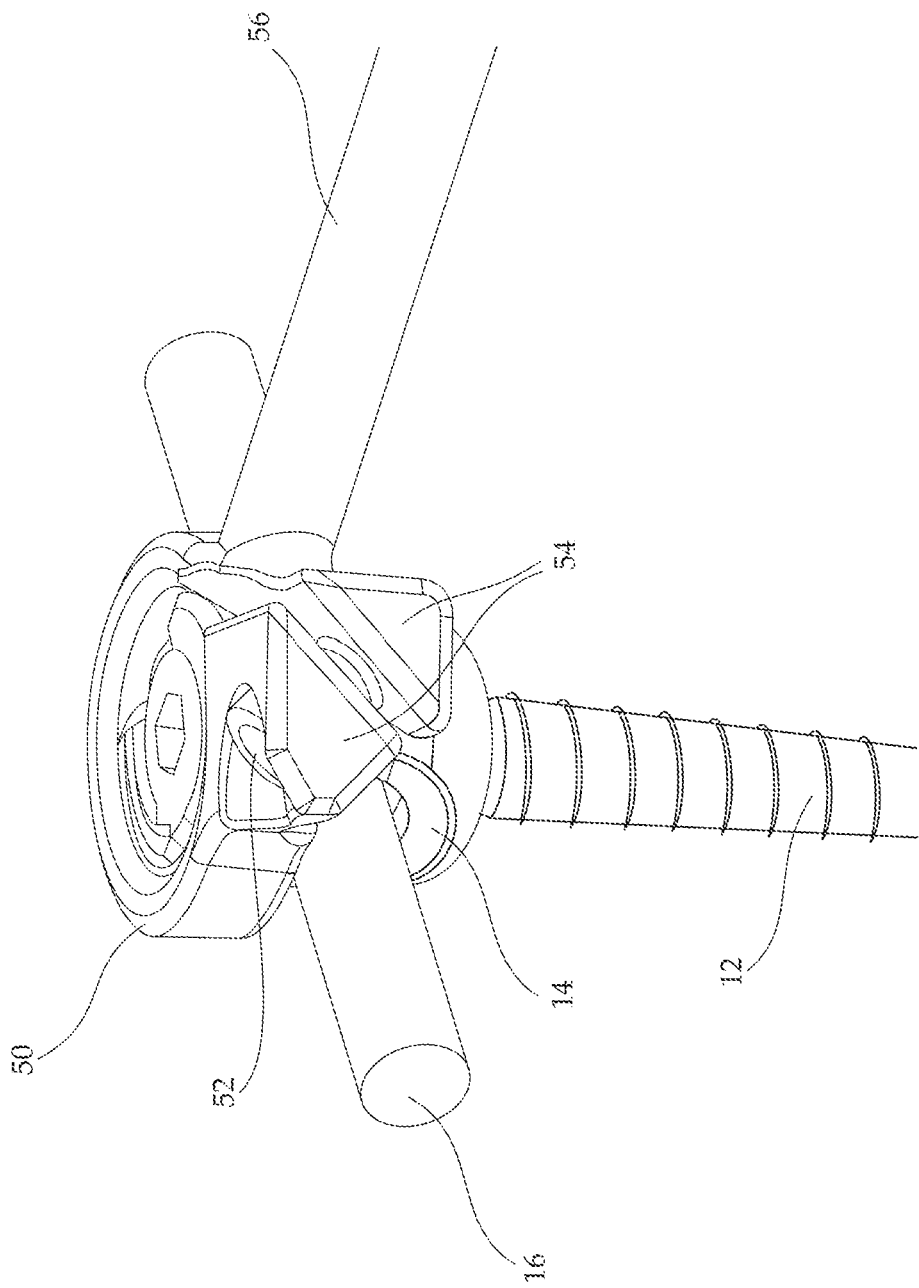
FIG. 8 is a more detailed illustration of the open ring and connector element of FIG. 7.

Reference is now made to FIGS. 7 and 8. In accordance with yet another embodiment of the invention the fastening portion includes an open ring 50 that fits over the polyaxial head 14 and a mechanical fastener 52 that fastens end portions 54 of the open ring 50 towards each other so as to clamp the open ring 50 onto the polyaxial head 14. The connector element includes a connecting member 56 that extends from open ring 50. The end portions 54 of the open ring 50 can be angled at an acute angle with respect to a top surface of the open ring 50.

Figure 9B:
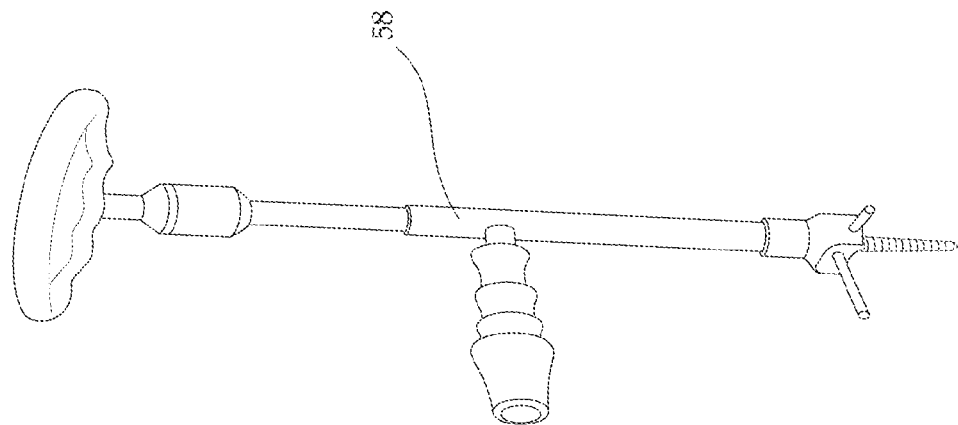
FIG. 9B is a pictorial illustration of a tool used to fasten the set screw of the existing polyaxial pedicle screw.
Figure 9A:
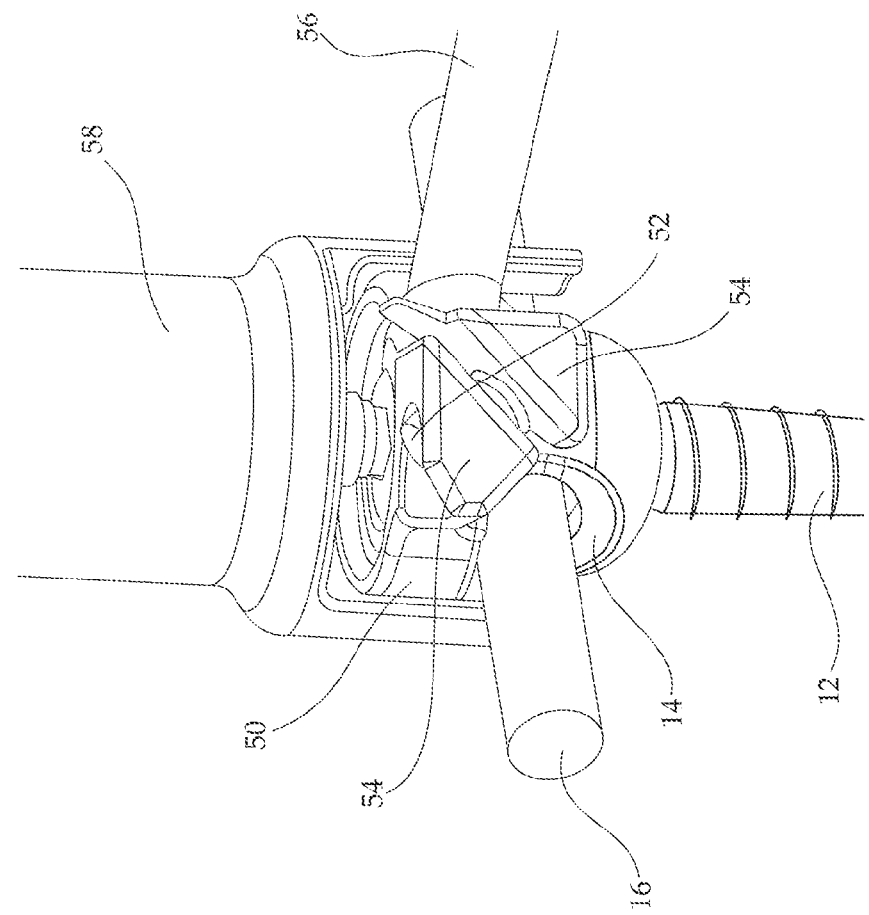
FIG. 9A is a pictorial illustration of fastening a set screw of the existing polyaxial pedicle screw while the fastener assembly of FIG. 7 is mounted on the existing polyaxial pedicle screw, in accordance with an embodiment of the present invention.
Figure 9D:
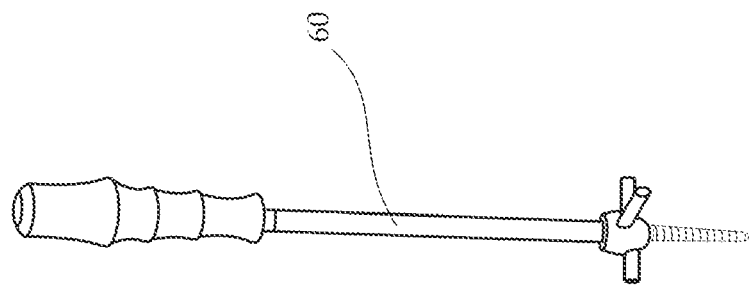
FIG. 9D is a pictorial illustration of a tool used to align the fastener assembly of FIG. 7 on the existing polyaxial pedicle screw.

Reference is now made to FIGS. 9A-9E. In FIG. 9A, a fastening tool 58 (also shown in FIG. 9B) is used to fasten the set screw of the existing polyaxial pedicle screw while the fastener assembly of FIG. 7 is mounted on the existing polyaxial pedicle screw.

Figure 9C:
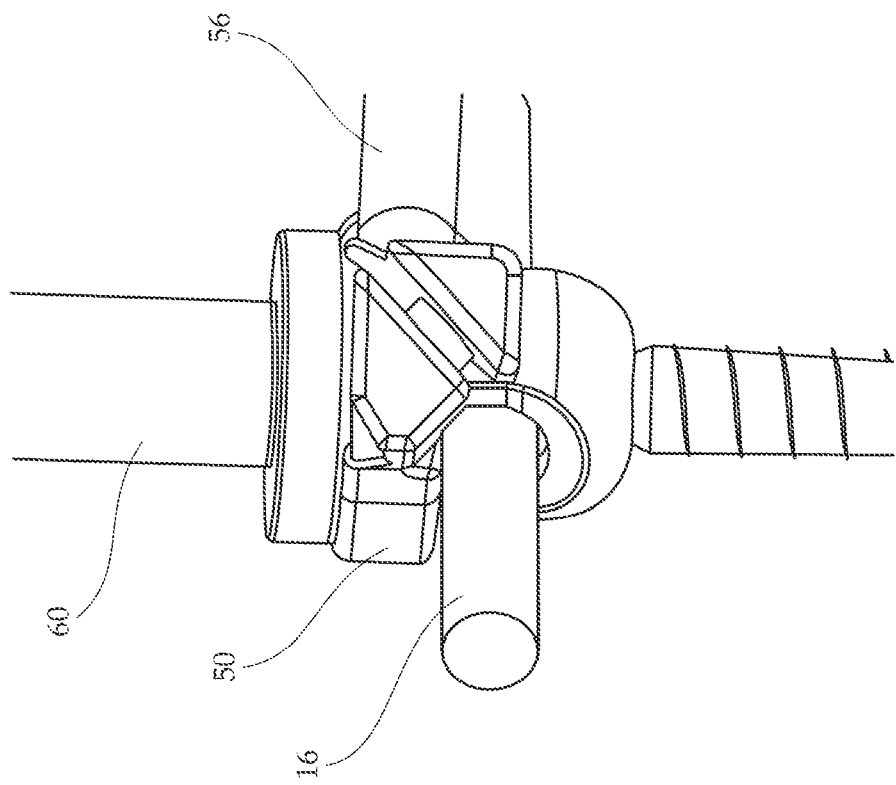
FIG. 9C is a pictorial illustration of aligning the fastener assembly of FIG. 7 on the existing polyaxial pedicle screw, in accordance with an embodiment of the present invention.

In FIG. 9C, a dedicated alignment tool 60 (also shown in FIG. 9D) is used to align the fastener assembly of FIG. 7 on the existing polyaxial pedicle screw 12.

In FIG. 9E, a tightening tool 62 is used to tighten the mechanical fastener of the fastener assembly of FIG. 7 so as to clamp the open ring 50 onto the polyaxial head 14.

It is appreciated that various features of the invention which are, for clarity, described in the contexts of separate embodiments, may also be provided in combination in a single embodiment. Conversely, various features of the invention which are, for brevity, described in the context of a single embodiment, may also be provided separately or in any suitable subcombination.

What is claimed is:

1. A fastener assembly comprising:
a spinal prosthesis comprising upper and lower elongate rods adapted for attachment to spinal structure of a patient, wherein said upper elongate rod extends from an upper plate, and said lower elongate rod extends from a lower plate, and a flexure assembly is positioned between said plates;
left and right pedicle screws mounted on left and right distal portions of each of said elongate rods for attaching said elongate rods to the spinal structure, each of said pedicle screws comprising a polyaxial head;
a left fastening portion fastened to said polyaxial head of said left pedicle screw of said lower elongate rod and a right fastening portion fastened to said polyaxial head of said right pedicle screw of said lower elongate rod, and wherein said left and right fastening portions are located at opposite ends of said lower elongate rod; and
a left connector element that extends from said left fastening portion in a direction transverse to said lower elongate rod and a right connector element that extends from said right fastening portion in a direction transverse to said lower elongate rod, said connector elements being connectable to another spinal structure, and wherein said left and right connector elements are located at opposite ends of said lower elongate rod; and
wherein at least one of said left and right fastening portions comprises a wedge ring and at least one of said corresponding left and right connector elements comprises a conical ring into which said wedge ring fits, said connector element comprising a connecting member that extends from said conical ring, wherein said wedge ring is sized to fit over said polyaxial head and said conical ring wedges said wedge ring onto said polyaxial head;
and further comprising a fastening tool operative to install said wedge ring and said connector element on at least one of said corresponding left and right pedicle screws, wherein said fastening tool comprises a pair of jaws into which said wedge ring and said connector element are inserted, a pair of handles connected to said jaws and an alignment indicator that indicates proper alignment of said connector element with said spinal prosthesis, wherein squeezing of said handles causes said conical ring to wedge said wedge ring onto said polyaxial head of each of said polyaxial screws.

2. The fastener assembly according to claim 1, wherein said wedge ring has a conical periphery with a top surface that has a larger outer diameter than a bottom surface thereof, and said conical ring has a top surface with a larger inner diameter than a bottom surface thereof, said larger outer diameter not being greater than said larger inner diameter.

3. The fastener assembly according to claim 2, wherein grooves are formed in said conical periphery of said wedge ring.

4. The fastener assembly according to claim 3, wherein at least one of said grooves is open at the top surface and closed at the bottom surface and at least another groove is closed at the top surface and open at the bottom surface.

* * * * *